United States Patent [19]

Abblard et al.

[11] 4,171,302

[45] Oct. 16, 1979

[54] PROCESS FOR PRODUCING N-SUBSTITUTED AMIDES

[75] Inventors: Jean Abblard, Saint-Didier au Mont d'Or; Michel Baudoin, Saint Fons, both of France

[73] Assignee: Philagro, France

[21] Appl. No.: 853,501

[22] Filed: Nov. 21, 1977

[30] Foreign Application Priority Data

Nov. 22, 1976 [FR] France ............................... 76 35864

[51] Int. Cl.² ............................................ C07D 205/10
[52] U.S. Cl. ......................... 260/239 A; 260/239.3 A; 260/326 R; 260/326 S; 260/326 N; 260/326 A; 260/326 HL; 260/326.5 S; 260/326.5 FM
[58] Field of Search ................. 260/326.5 FM, 326 R, 260/326 S, 326 N, 326 A, 326 HL, 326.5 S, 239.3 A, 239 A

[56] References Cited

U.S. PATENT DOCUMENTS

| 3,338,919 | 8/1967 | Nield | 260/326.5 FM |
| 3,431,276 | 3/1969 | Nield | 260/326.5 FM |

*Primary Examiner*—Jose Tovar
*Attorney, Agent, or Firm*—Robert E. Burns; Emmanuel J. Lobato; Bruce L. Adams

[57] ABSTRACT

A process of preparing a N-substituted imide as disclosed, which is carried out in accordance with the equation:

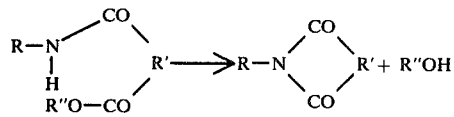

wherein R is an alkyl radical containing 1 to 8 carbon atoms, or an aryl radical having 1 or 2 phenyl rings bearing up to 5 substituents selected from the group consisting of 1 to 3 atoms of halogen, 1 to 2 nitro, amino, or hydroxy groups, 1 to 4 alkyl radicals, and 1 to 2 alkoxy or alkylthiol radicals each containing 1 to 4 carbon atoms, or a hexyl radical, optionally substituted;

R' is a single bond or a hydrocarbon chain containing from 1 to 4 carbon atoms, in which two contiguous carbons may belong to a phenyl ring, said hydrocarbon chain being saturated or unsaturated and optionally substituted and R" is a hydrogen atom, an alkaline metal atom, an ammonium atom or a lower alkyl having 1 to 4 carbon atoms, wherein the cyclization of the amic acid, R—NH—CO—R'—COOR" is carried out in the presence of a mixed catalyst which results from the association of the formula, A B, in which A is a strong inorganic or organic acid and B is a Lewis base.

29 Claims, No Drawings

PROCESS FOR PRODUCING N-SUBSTITUTED AMIDES

BACKGROUND OF THE INVENTION

This invention relates to a new process of preparing imides substituted on the nitrogen from amic acids as well as a process for the preparation of these imides from a di-acid or its anhydride and from a primary amine.

There is extensive literature on this subject. In accordance with Searle (C.A. 42 7340c (1948)), numerous authors have effected the preparation of N-imides, in particular N-aryl maleimides, by the cyclicizing dehydration of a maleamic acid in the presence of acetic anhydride as dehydrating agent and of alkaline acetate as catalyst, in accordance with the equation:

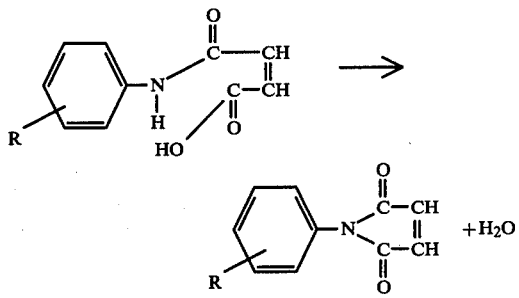

This reaction is, as a matter of fact, used as second step in the preparation of the above N-arylimides from an aniline and maleic anhydride. These two reagents give the intermediate, maleamic acid in a first step in accordance with the reaction:

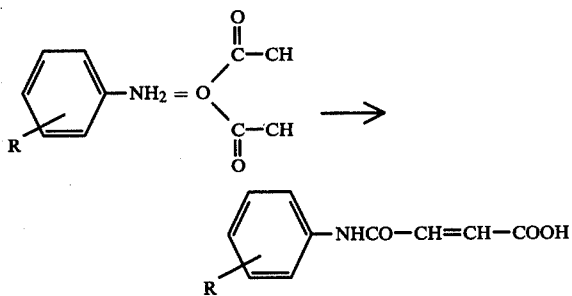

This reaction takes place readily, the yields being generally greater than 90%.

This method, which was intended to be a general method, has encountered numerous failures, since the ease of reaction depends largely on the substituents borne by the phenyl ring. While, for example, yields of 70 to 90% are obtained when the substituents are chlorine atoms, they become average or even low when the phenyl ring is substituted by nitro, methyl, methoxy or ethoxy, or hydroxy groups or when the imide is substituted on the nitrogen by a lower alkyl radical.

To this there must be added the lack of reliability of the method, as illustrated by the great differences in yield indicated by various authors for one and the same product.

Finally, this method comprises two steps and provides impure, poorly crystalline products, the impurities not being capable of being eliminated by recrystallization. Such a process therefore absolutely does not constitute an industrial process.

Among the processes proposed in order to solve these problems, the one described in French Patent No. 1 418 336 constitutes an advance. This process consists in effecting the dehydration in solvent medium of an alpha or beta amic acid and particularly maleamic acid, no longer by means of a dehydrating agent but rather in the presence of 0.01 to 20% by weight, referred to the acid, of a catalyst formed of a strong acid such as sulfuric acid, or chlorosulfonic or organosulfonic acid, in particular paratoluene sulfonic acid, phosphoric acid and organophosphonic acid, particularly benzene phosphonic acid. This process leads to average crude yields of more than 50% while not exceeding 90%, but has several serious drawbacks. First of all, the crude products are very impure (from 5 to 20% impurities), and they must then be purified by chromatography on a column of alumina, which cannot be extrapolated industrially. Furthermore, the reaction times although shortened are still long. The example of the N-2-chlorophenylmaleamic acid of the patent cited, for which times of an hour are given, should not deceive one since its cyclization is particularly easy whatever the process contemplated. It should furthermore be pointed out that even in the case of this product, this reaction time may vary from one hour to nine and a half hours depending on the catalyst. As a matter of fact, when such a process is applied to a maleamic acid obtained from an aniline which is polymethylated on the ring, such as mesidine, in the presence of an effective catalyst such as paratoluene sulfonic acid, the time required is ten hours, which clearly shows the limitations of the process.

It has also been proposed (see West German Unexamined Application for Patent No. 2 100 800) to catalyze the dehydration of a succinamic or maleamic acid which has been obtained by condensation of succinic or maleic acid on an aromatic amine, the catalyst being produced by a strongly basic compound of the hydroxide or alcoholate type, of ammonium, alkaline or alkaline earth metal or tertiary amine, preferably triethyl amine.

In accordance with said patent, the process employs periods of time not in excess of four hours, and gives yields of the order of 80 to 90%, but has the serious defect of producing an impure product. Furthermore, its illustration is limited since, based on substituents in 3 or 3,5 position on the phenyl ring, and gives a single example of a monomethyl or monomethyloxyl product on the ring.

The application of this process to 2,4,6-trimethylphenylmaleamic acid has led to a very impure crude product (very highly colored), its melting point showing a difference of 10° C. from the value for the pure product. Finally, this patent describes essentially xylene as solvent, which favors the reaction velocity, and gives an example in which when this solvent is replaced by toluene, again under reflux and therefore at lower temperature, the reaction cannot take place. Toluene is not included in the list of suitable solvents. This clearly shows the limitation of this process.

SUMMARY OF THE INVENTION

The present invention now proposes a new process of preparing, in a single step, N-substituted imides which combine, while improving, the advantages of the previously mentioned processes, particularly yields which are almost quantitative and very short reaction times, while furthermore overcoming their main defect by providing a crude product of very high purity.

More specifically, the invention concerns a process of preparing an imide substituted on the nitrogen, of the general formula

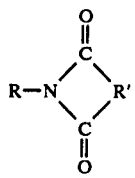

in which:

—R is either an alkyl radical containing 1 to 8 carbon atoms, or an aryl radical having one or two phenyl rings possibly bearing 1 to 5 substituents selected from the group consisting of 1 to 3 atoms of halogen, 1 to 2 nitro, amino, or hydroxy groups, 1 to 4 alkyl radicals, and 1 to 2 alkoxy or alkylthiol radicals each containing from 1 to 4 carbon atoms, or else a hexyl radical, possibly substituted;

—R' is a single bond or a hydrocarbon chain, whether saturated or unsaturated and possibly substituted, containing 1 to 4 carbon atoms, two contiguous carbons possibly being part of a phenyl ring, by cyclization of an amic acid of the formula:

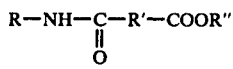

in which:

—R and R' have the same meaning as above,

—R'' is a hydrogen atom, an alkaline metal atom, an ammonium group or a lower alkyl having 1 to 4 carbon atoms, in accordance with the equation:

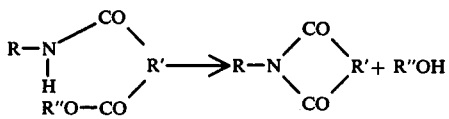

characterized by the fact that the reaction is carried out in the presence of a mixed catalyst resulting from the combination of formula:

AB is which A is a strong inorganic or organic acid and B is a Lewis base.

The catalyst in accordance with the invention is prepared by mixing a strong inorganic or organic acid with a Lewis base either before the mixing with the reagents or within the reaction medium.

By strong inorganic or organic acid there is meant a mono- or poly acid of a $pK_A$ in water which is at most equal to 3, such as sulfuric acid, organosulfonic acids, and particularly paratoluenesulfonic acid, methane sulfonic acid, phosphoric acid and the organic acids derived from phosphorus, in particular the monoalkyl or aryl phosphonic acids, such as in particular methylphosphonic, benzene-phosphonic or naphthalene sulfonic acid or else hydrochloric acid or a strong carboxylic acid such as di- and trihalo- (and particularly chloro- and fluoro-) acetic or propionic acid or an ethylenic acid, such as maleic or fumaric acid. The preference is given to sulfuric and paratoluene sulfonic acids.

By Lewis base there is understood a compound which has at least one heteroatom, in particular oxygen, sulfur, or nitrogen, capable of furnishing a pair of electrons. The preferred compounds contain in addition to the electrons, a double or triple bond. As examples, mentioned may be made of mono- and di-methylformamide, dimethyl acetamide, acetone, di-methylsulfoxide, acetonitrile, N-methylpyrrolidone and mesityl oxide. Dioxane and tetrahydrofuran can also be used.

These two components, a strong acid and a Lewis base, are mixed in quantities which depend on the number of acid functions in the strong acid. The equivalent of the Lewis base corresponds to at least one of these functions. For example, in the case of a monoacid such as paratoluene sulfonic acid, there will be a single type of complex formed by an equimolar mixture of the Lewis base and the acid. In the case of a diacid such as sulfuric acid, one can have two types of complexes, and the Lewis base can be present in the form of one or two molar equivalents. These precise proportions correspond to compounds having well-defined physical-chemical properties which are different from those of each of the components taken individually. Thus it has been possible to isolate and characterize the "1:1 sulfuric acid/dimethylformamide" and "1:1 paratoluene sulfonic acid-dimethylformamide" complexes by nuclear magnetic reasonance. In practice, an equilibrium is frequently produced between the two types (1:1 and 1:2 mixtures) of complexes so that the ratio of the components in the reaction medium is no longer an exact number. Stated differently, in the case of a di-acid, the molar proportion of Lewis base to strong acid may be between 1 and 2. More generally, the molar ratio of the components, Lewis base and acid of the catalyst, may advantageously be between 0.1 and 2.

These proportions can be modified. The applicant has, however, found that an excess of the Lewis base can improve the yield. On the other hand, an excess of acid has a definitely unfavorable effect.

The catalyst of the invention is definitely active even in very small dose, practically as soon as it is present in a molar ratio of 0.01 with respect to the initial amic acid. Ratios of between 0.25 and 2 can be used, preference being given to ratios of between 0.05 and 0.5. Higher ratios do not produce any greater catalytic effect and are therefore without interest from an economic standpoint.

More precisely, the molar ratio of the acid part of the catalyst with respect to the initial amic acid is between 0.01 and 10, and preferably 0.1 to 1. On the other hand, the molar ratio of the Lewis base portion of the catalyst with respect to the initial amic acid is at least equal to 0.01. If the reaction is carried out in a solvent of a nature different from the Lewis base, the upper limit of the ratio may be fixed at about 1. However, if an excess of the Lewis base can serve as inert solvent for the reaction, the ratio may reach values of up to about 100.

The reaction in accordance with the invention is carried out at a temperature of between 80° C. and 180° C. and preferably between 100° and 150° C. Below 80° C., the reaction is slow, making the process uneconomical. On the other hand, excessively high temperatures favor the appearance of secondary reactions.

Moreover, the process in accordance with the invention can be carried out in the absence or in the presence of solvent. In the former case, it is clear that the Lewis base does not act as solvent with respect to the reagents either by nature or by reason of the excessively small quantities referred to said compounds.

One can also carry out the process of the invention in an inert solvent. As suitable solvent mention may be made of the aromatic hydrocarbons possibly chlorinated, or of the aliphatic hydrocarbons, possibly chlorinated.

Particularly interesting results have been obtained with toluene and xylene, preference being given to the former due to their ability to form, with water, an azeotrope which eliminates the water from the medium during the course of the reaction. Within this family mention may be made of benzene and toluene, alone or in mixture, xylene and chlorobenzene.

It should also be noted that the inert solvent may consist of an excess of the Lewis base over the catalytic quantity defined above.

The applicant has found that the use of the solvent has the effect of increasing the yields which nevertheless are already high in the absence of solvent, even when large quantities of reagents are employed, this being so up to practically quantitative values.

On the other hand, the addition of solvent increases the volume of the reaction medium and therefore decreases the coefficient of filling of the apparatus. The solvent-less process is more interesting from this latter point of view, but has the slight drawback of providing yields which are lower although still being definitely greater than 80%, and leads to products which are slightly less pure than previously.

Due to the power of the catalytic effect of the complexes in accordance with the invention, the reaction time rarely exceeds 5 hours and is generally between half an hour and 2 hours. The difference is due essentially to the amount of catalyst introduced and the nature of the solvent, as well as the nature of the initial amic acid.

The above process has been described for amic acids as defined. In industrial practice, these amic acids are not prepared separately but one starts from a mixture of acid HOCO—R'—COOH or its anhydride and from the primary amine R—NH$_2$, the condensation to form amic acid taking place without difficulty with a high yield so that the two reactions take place in a single step. Most of the tests reported in the examples were furthermore carried out in this manner.

The tests, with two exceptions, concern 2,4,6-trimethylphenyl maleamic acid. This compound is a typical example of a compound which is difficult to obtain satisfactorily on an industrial scale from mesidine and maleic acid by the known process, due in particular to the necessity of two steps, the obtaining of an impure poorly crystallized product which cannot be purified by recrystallization, and the handling of a large quantity of acetic anhydride. However, it will be clearly understood that this is not a limitative character and that the amic acids defined above can be cyclicized by the method of the invention.

It should be noted that the operations described below were carried out with a reactor equipped with a Dean Stark apparatus which makes it possible to collect the water which has formed during the reaction and thus to follow-up the course of the reaction.

EXAMPLES 1-7

0.5 mol of maleic anhydride, 0.4 L of toluene and a variable amount, referred to mesidine, of the mixture in situ of sulfuric acid and dimethylformamide is charged into the reactor.

0.5 mol of mesidine are poured in within the course of 5 minutes. There is an exothermic formation of maleamic acid which causes the temperature of the reaction medium to increase to 100° C. The mixture is then brought to reflux until obtaining a constant amount of water in the flask of the Dean Stark apparatus. The toluene solution is filtered to isolate any insoluble byproduct, washed with water, and concentrated under reduced pressure. The solid obtained is weighed and analyzed without purification. Analysis shows that it is N(2,4,6-trimethylphenyl)maleimide. Furthermore, the wash water of the organic phase is alkalinized and extracted with toluene which makes it possible after concentration to obtain the mesidine which may form during the reaction from the maleamic acid.

The following table gives, for each molar ratio of catalyst to mesidine and therefore of catalyst to maleamic acid, the reaction time, the yield of crude product, the melting point of the crude product (that of pure N(2,4,6-trimethylphenyl maleimide) is 99°–100° C.), its concentration, and the actual yield of pure product as well as the weight of mesidine recovered, expressed in percentage referred to the quantity used, and the percentage by weight of insoluble product.

TABLE I

| Examples | H$_2$SO$_4$ DMF 1:1* | Reaction time | Yield % | Melting point °C. | Concentration % | Corrected yield % | Mesidine recovered in % of that used | Insoluble matter % imide expected |
|---|---|---|---|---|---|---|---|---|
| 1 | 2.5% | 5H 15 | 74.5% | 95° C. | 97% | 72.3% | 0 | 6.5% |
| 2 | 5% | 2H 30 | 85.6% | 97° C. | 95% | 81.3% | 0 | 5.2% |
| 3 | 50% | 1H 15 | 93% | 98° C. | 99% | 92% | 0 | 2.1% |
| 4 | 25% | 1H | 93% | 99° C. | 100% | 93% | 0 | — |
| 5 | 50% | 1H | 91% | 99° C. | 98% | 89% | 4% | — |
| 6 | 100% | 1H | 92% | 99° C. | 100% | 92% | 6% | — |
| 7 | 200% | 2H 15 | 91% | 98° C. | 100% | 91% | 0 | — |

This table clearly shows, on the one hand, that with even a dose of only 0.025 mol per mol of mesidine, the reaction time is decreased (without catalyst the reaction makes 24 hours), the melting point approaches that of the pure product and the yield improves, already exceeding 70%. With 0.01 mol of complex, the reaction time (1¼ hour) and the corrected yield (92%) are already optimum and practically do not vary any more with larger amounts of complex.

Under these conditions, the optimal region is between 0.25 and 1 mol per mol of mesidine. It covers very short reaction times (1 to 2 hours) combined with very high yields (greater than 90%) of a product of high purity. The byproducts formed comprise essentially on the one hand a product insoluble in toluene, less of which is formed the faster the reaction and on the other hand, for 0.5 and 1 mol of complex, mesidine.

EXAMPLES 8 TO 11

The same procedure is used as in Example 6 corresponding to the use of 1 mol of H$_2$SO$_4$/DMF (1:1) catalyst mixture per mol of mesidine or maleamic acid, as compared with the case in which the catalyst is formed solely either of sulfuric acid or of dimethylformamide.

Examples 8 and 9 differ by the fact that in the former one starts from mesidine and maleic anhydride while in the latter one starts from the corresponding maleamic acid.

The results are set forth in the following Table:

TABLE 2

| Examples | Catalyst | Reaction time | Yield % | Melting point °C. | Concentration % | Corrected yield % | Mesidine recovered in % of that used | Insoluble matter % imide expected |
|---|---|---|---|---|---|---|---|---|
| 8 | H$_2$SO$_4$ alone | 8H 15 | 63% | 98° C. | 97.2% | 61.2% | 28% | 0 |
| 9 | H$_2$SO$_4$ alone | 6H 10 | 55% | 94° C. | 95.6% | 52.6% | 43% | 0 |
| 10 | DMF alone | 7H 16 | 70.7% | 95° C. | 92% | 65% | 0 | 21.5% |
| 11 | H$_2$SO$_4$/DMF (1:1) | 1H | 92% | 99° C. | 100% | 92% | 0 | 0 |

From this table it can be concluded that referred to each of the components of the catalyst mixture used by themselves, the mixture makes it possible unexpectedly simultaneously to considerably reduce (from 6–8 hours to 1 hour) the reaction time and to increase the corrected yield of a crude product of improved purity by about 30–50% up to high levels. It is to be noted that with sulfuric acid alone, the maleamic acid suffers, concurrently with its dehydration, a substantial hydrolysis into mesadine and maleic acid, which may explain the low yields obtained by this prior-art process. The difference is such that one can easily note the particular suitability of the process of the invention for industrial use.

EXAMPLES 12 to 16

One proceeds in the same manner as in Examples 1 to 5, except that as catalyst there is used a mixture of two equivalents of dimethylformamide to one equivalent of sulfuric acid.

The results are set forth in the following table:

TABLE 3

| Examples | H$_2$SO$_4$ . DMF 1:2* | Reaction time | Yield % | Melting point C. | Concentration % | Corrected yield % | Mesidine recovered in % of that used | Insoluble matter % imide expected |
|---|---|---|---|---|---|---|---|---|
| 12 | 2.5% | 4H 15 | 87% | 95°–96° C. | 95.5% | 83% | — | 6% |
| 13 | 5% | 2H 10 | 93% | 97° C. | 97.5% | 90.7% | — | 2.8% |
| 14 | 12.5% | 1H | 87.5% | 99°–100° C. | 100% | 87.5% | — | 0.8% |
| 15 | 25% | 1H | 92.5% | 100° C. | 100% | 92.5% | — | 0.26% |
| 16 | 50% | 55 mn | 97% | 100° C. | 100% | 97% | — | — |

*molar % of complex H$_2$SO$_4$ DMF (1:2) referred to the mesidine used

These results show that this type of complex very powerfully catalyzes the cyclicizing dehydration reaction with a slight but definite superiority in all fields over the corresponding results of Examples 1 to 5 using an H$_2$SO$_4$DMF (1:1) complex.

We may note in particular that with the smallest concentration of 0.025 mol of complex, the corrected yield is already 83%. On the other hand, for 0.5 mol of complex per mol of maleamic acid, the corrected yield is 97% for one hour of reflux and a concentration of 100% crude product.

EXAMPLES 17 AND 18:

Reaction for Maleic Acid

One proceeds in the same manner as in Examples 4 and 16, but replacing the maleic anhydride by an equivalent amount of maleic acid.

The results are set forth in the following table:

TABLE 4

| Examples | H$_2$SO$_4$ DMF referred to molar | % molar complex/ mesidine | Reaction time | Yield % | Melting point | Concentration % | Corrected yield % | Mesidine recovered in % of that used | Insoluble matter % imide expected |
|---|---|---|---|---|---|---|---|---|---|
| 17 | 1.1 | 25% | 1H 50 | 74.6% | 98° C. | 96.5% | 72% | 15.7% | 0 |
| 18 | 1.2 | 50% | 1H 20 | 76.6% | 97° C. | 96.6% | 74% | 14.8% | 0 |

EXAMPLES 19 TO 29:

Use of 1:1 Complex of DMF with Various Strong Acids

One proceeds in the same manner as in Example 3, that is say with 0.1 mol of catalyst complex per mol of mesidine, except that the sulfuric acid is replaced by an equimolar quantity of another strong acid.

The results of the tests are set forth in the following table:

TABLE 5

| Examples | Acid DMF (1:1) % | Reaction time | Yield % | Melting point °C. | Concentration % | Corrected yield | Mesidine recovered as % of that used | Insoluble matter % imide expected |
|---|---|---|---|---|---|---|---|---|
| 19 | paratoluene sulfonic 10% | 2H 30 | 83.0% | 98° C. | 98.0% | 81.3% | 0.6% | 0 |
| 20 | paratoluene sulfonic | 1H | 91.6% | 98° C. | 96.9% | 88.7% | 0.1% | 2% |

TABLE 5-continued

| Examples | Acid DMF (1:1) % | Reaction time | Yield % | Melting point °C. | Concentration % | Corrected yield | Mesidine recovered as % of that used | Insoluble matter % imide expected |
|---|---|---|---|---|---|---|---|---|
| 21 | 10% paratoluene sulfonic | 35 min | 99.4% | 94°–95° C. | 98.9% | 98.3% | 1.5% | 0 |
| 22 | 25% trifluoroacetic | 2H 15 | 92.0% | 86° C. | 92.0% | 84.6% | 0 | 5% |
| 23 | 10% trifluoroacetic | 50 min | 99.5% | 88° C. | 90.5% | 90.0% | 0 | 1.7% |
| 24 | 25% phosphoric | 3H | 84.5% | 90° C. | 86.4% | 73.0% | 0 | 10.0% |
| 25 | 10% phosphoric | 2H 30 | 89.5% | 86° C. | 90.3% | 81.0% | 0 | 0.6% |
| 26 | 25% maleic | 5H | 75.0% | 93°–94° C. | 94.0% | 70.5% | 0 | 11.0% |
| 27 | 10% maleic | 1H 50 | 74.6% | 98° C. | 96.5% | 72.0% | 15.7% | 0 |
| 28 | 25% dichloroacetic 10% | 4H 15 | 73.5% | 93° C. | 90.1% | 66.2% | 0 | 7.0% |
| 29 | trichloroacetic 25% | 3H 10 | 98.6% | 82° C. | 66.7% | 65.7% | 1.2% | 0.4% |

From this table it can be concluded that under these conditions, paratoluene sulfonic acid gives the best results. The results obtained with the trifluoro- and trichloroacetic, dichloroacetic, phosphoric and maleic acids are poorer, but prove that the sulfuric acid tested in the preceding examples does not play its conventional role of dehydrating agent but rather the role of catalyst.

EXAMPLES 30 AND 31

One proceeds in the same manner as in Example 2, using, as catalyst, in an amount of 0.05 mol per mol of mesidine, paratoluene sulfonic acid (PTS) alone, in accordance with the process of French Patent 1 418 336, and its 1:1 complex with dimethylformamide (DMF) in accordance with the invention. Furthermore, 10 mols of mesidine and maleic anhydride are used.

Under these conditions, it is noted that the reaction takes 8 hours in the first case as compared with only two hours and 30 minutes in the second case, the yield is lower than the 84% obtained with the complex, and the crude product is colored and very impure, while it is of excellent purity (melting point of 98° C.) in the second case.

This clearly shows the considerable unforeseeable improvement made by the process of the invention as compared with the prior process.

EXAMPLES 32 TO 48

One proceeds in the same manner as in Examples 1 and 2, using respectively 0.05 and 0.25 mol per mol of mesidine of a catalyst complex in which the strong acid is sulfuric acid and the Lewis base is no longer dimethylformamide but acetonitrile, acetone, N-methylpyrrolidone, dimethylsulfoxide, monoethylformamide, mesityl oxide, dioxane and tetrahydrofuran respectively.

The results are set forth in the following table:

TABLE 6

| Examples | H₂SO₄ . base %* | Reaction time | Yield % | Melting point | Concentration % | Corrected yield % | Mesidine recovered as % employed | Insoluble matter as % imide expected |
|---|---|---|---|---|---|---|---|---|
| 32 | acetonitrile (1:1) 5% | 4H 40 | 74.5% | 97° C. | 94% | 70% | 0 | 4.7% |
| 33 | acetonitrile (1:1) 25% | 1 H | 81.8% | 94° C. | 87,6% | 71.6% | 13% | 9.4% |
| 34 | acetone (1:1) 5% | 4 H | 70.7% | 96° C. | 93% | 65.7% | 0 | 8.5% |
| 35 | acetone (1:1) 25% | 1 H | 80.4% | 100° C. | 100% | 80.4% | 12% | 0 |
| 36 | N-methyl pyrrolidone (1:1) 5% | 2H 20 | 90.0% | 97° C. | 96.5% | 86.8% | 0 | 4.0% |
| 37 | N-methyl pyrrolidone (1:1) 25% | 50 mn | 96.5% | 100° C. | 100% | 96.5% | 1% | 0 |
| 38 | N-methyl pyrrolidone (2:1) 25% | 30 mn | 98.6% | 100° C. | 100% | 98.6% | 0 | 0 |
| 39 | Dimethylsulfoxyde (1:1) 5% | 2 H | 92.0% | 97° C. | 98.5% | 89.6% | 0 | 5.6% |
| 40 | Dimethylsulfoxyde | 40 mn | 89.0% | 97° C. | 97.9% | 87.1% | 1.4% | 0.9% |

TABLE 6-continued

| Examples | H$_2$SO$_4$ . base %* | Reaction time | Yield % | Melting point | Concentration % | Corrected yield % | Mesidine recovered as % employed | Insoluble matter as % imide expected |
|---|---|---|---|---|---|---|---|---|
| 41 | (1:1) 25% mesityl oxide | 2H 30 mn | 77.5% | 94° C. | 92.3% | 71.5% | 1% | 14.5% |
| 42 | (1:1) 5% mesityl oxide | 1H 30 mn | 72.5% | 95° C. | 98.4% | 71.3% | 1.2% | 0 |
| 43 | (1:1) 25% Monomethyl formamide | 2 H | 88.0% | 93° C. | 88.1% | 77.5% | 0 | 7.1% |
| 44 | (1:1) 5% Monomethyl formamide | 40 mn | 97.3% | 96°–97° C. | 91.9% | 89.4% | 3.7% | 0 |
| 45 | (1:1) 25% Dioxane 10% | 2 H | 91.2% | 81° C. | 84.% | 76.6% | 5.0% | 4.2% |
| 46 | Dioxane 25% | 1H 10 | 81.4% | 83° C. | 89.0% | 72.4% | 10.3% | 6.5% |
| 47 | Tetrahydrofuran 10% | 2H 10 | 87.7% | 85° C. | 92% | 80.7% | 1.5% | 4.7% |
| 48 | Tetrahydrofuran 25% | 1H 10 | 78.0% | 76° C. | 86% | 67.0% | 9.7% | 8.0% |

*molar % of base H$_2$SO$_4$ complex referred to the mesidine used

These results clearly show the excellent behavior of the N-methylpyrrolidone even in the low dose, but also the interesting behavior of the other Lewis bases.

EXAMPLE 49

One proceeds in the same manner as in Example 4, except that there is used 0.25 mol of sulfuric acid dimethylformamide complex per mol of mesidine and that the toluene is replaced as inert solvent by xylene.

Under these conditions, it is observed that the reaction is completed in 12 minutes, namely 1/5 as long as with toluene. On the other hand, the yield is lower (85% as compared with 93%). This can be explained by the fact that as the reaction is so fast the water produced cannot be removed, even with the Dean Stark apparatus, so that the water in its turn hydrolyzes the maleamic acid in form mesidine.

EXAMPLES 50 TO 56

One proceeds in the same manner as in Examples 4, 5 and 6 on the one hand, that is to say in the presence of a 1:1 sulfuric acid/dimethylformamide catalyst complex and in the same manner as in Examples 15 and 16, on the other hand, that is to say in the presence of a 1:2 sulfuric acid/dimethylformamide complex with furthermore a test with a 1:1 complex/mesidine molar ratio, except that the reagents are used without solvent and the reaction is maintained for one hour at 100° C.

The results are set forth in the following table:

ever, they are still very good and have the additional advantage, which is important from an industrial standpoint, of a high coefficient of filling of the reactor.

EXAMPLE 57

One proceeds as in Example 4, except that only 0.5 mol of butylamine is poured onto a solution of 0.55 mol of maleic anhydride in 300 ml of toluene containing 0.167 mol, namely 30 mol%, of 1:1 H$_2$SO$_4$/DMF complex.

The mixture is kept under reflux for five hours. After filtration and concentration under reduced pressure a liquid corresponding to N-butylmaleimide, conformity being established by means of the NMR spectrum, is obtained in a yield of 66%.

EXAMPLE 58

One proceeds in the same manner as in Example 39 on 20 mols of mesidine, 20 mols of maleic anhydride, using as catalyst a mixture in situ of 10 mol of sulfuric acid and 10 mols of dimethylformamide.

The mesidine is poured in 20 minutes so that the temperature is maintained at 110° to 115° C. The reaction medium is maintained at this temperature for 40 minutes. Thereupon it is cooled and poured into 5 L of water. The 2,4,6-trimethylphenylmaleimide crystallizes; it is then washed and dried. A crude product of good purity, of a concentration of 97%, of a melting point of 98° C., is obtained in a yield of 86%.

TABLE 7

| Examples | Nature of the complex | molar % complex/mesidine | Yield | Melting point | Concentration % | Corrected yield | Mesidine recovered as % of that used | Insoluble matter % imide expected |
|---|---|---|---|---|---|---|---|---|
| 50 | H$_2$SO$_4$ . DMF 1:1 | 25% | 83% | 96° C. | 96.2% | 80% | 11.55% | 0 |
| 51 | | 50% | 86% | 97° C. | 95.4% | 82% | 10.7% | 0 |
| 52 | | 100% | 74.5% | 98° C. | 98.6% | 73.5% | 20.9% | 0 |
| 53 | H$_2$SO$_4$ . DMF 1:2 | 10% | 91.4% | 91° C. | 81.5% | 74.5% | 5.9% | 0 |
| 54 | | 25% | 87.7% | 98° C. | 97% | 85% | 6.4% | 0 |
| 55 | | 50% | 87.2% | 98° C. | 97% | 84.5% | 8.9% | 0 |
| 56 | | 100% | 79% | 96° C. | 94.4% | 74.5% | 15.4% | 0 |

These results show that the yield and the purity are slightly inferior to those obtained with toluene. How- This example clearly shows that the results found for small amounts are found in larger (sic) and that the process of the invention without solvent is readily industrializable.

EXAMPLE 59

An apparatus equipped with a Dean Stark distillation device for eliminating the water as it is formed is employed.

100 mols of maleic anhydride, 60 liters of toluene and 30 mols of dimethylformamide are introduced into a reactor. The sulfuric acid (30 mols) is then poured in, followed by the mesidine (100 mols) over the course of 15 minutes, the reaction medium being maintained at 75° C. with agitation. It is then refluxed for 1½ hours, whereupon the medium is cooled. The sulfuric acid/dimethylformamide complex is withdrawn whereupon the toluene solution is washed and concentrated under reduced pressure. The pure dry imide is thus obtained.

Under these conditions, a very pure crude product (melting point 99° C.) is obtained in a yield of 92%. This clearly shows the great suitability of the process for use on an industrial scale.

EXAMPLE 60

Very close results are obtained when one starts in all the preceding examples from 2,4,6-trimethylphenyl maleamic acid instead of the mixture of maleic anhydride or acid and mesidine.

EXAMPLES 61 TO 74

0.05 mol of an amic acid (maleamic acid in the case of Examples 61 to 68, succinamic acid in the case of Examples 69 to 74) or the corresponding mixture of anhydride and aniline are introduced into an apparatus equipped with a Dean Mark distillation device. 100 mL of toluene or benzene are then added as solvent and 0.025 mol of 1:1 $H_2SO_4$/DMF complex, namely in a molar ratio of 50% with respect to the amic acid. The temperature rises slightly. It is heated under reflux and the azeotrope distilled. The reaction time varies depending on the nature of the aniline.

The reaction mixture is then washed with water until neutral and dried over sodium sulfate.

After evaporation of the solvent a crude product is obtained which is recrystallized from a suitable solvent (alcohol).

The indicated structure of the compounds was confirmed by NMR spectrography.

The conditions and results are set forth in the following tables:

TABLE 8

Maleimides

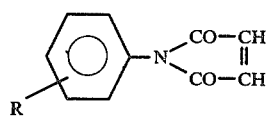

| Examples | R (substituted phenyl) | Solvent used | Reaction time | Melting point °C. | Yield |
|---|---|---|---|---|---|
| 61 | 2,4,6-tri(CH₃), 4-CH(CH₃)₂ position O | Toluene | 1H 30 | 102.2° C. | 89.6% |
| 62 | 2,4,6-tri(CH₃), 4-C(CH₃)₃ | Toluene | 1H 15 | 175.7° C. | 92.4% |
| 63 | NO₂, F | Benzene | 1H 15 | 124.4° C. | 87.2% |
| 64 | 2,3,5,6-tetra(CH₃) | Toluene | 4H | 145.2% | 89.0% |

TABLE 8-continued

Maleimides

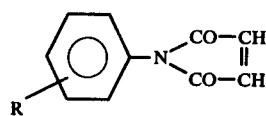

| Examples | R | Solvent used | Reaction time | Melting point °C. | Yield |
|---|---|---|---|---|---|
| 65 | 2,4,6-tri(isopropyl) | Toluene | 1H | 154.5° C. | 90.7% |
| 66 | 2,4-dimethoxy (OCH₃, CH₃O) | Benzene | 1H 30 | 146.0° C. | 75.3% |
| 67 | 3,5-dimethoxy (CH₃O, CH₃O) | Benzene | 8H 30 | 121.8° C. | 64.3% |
| 68 | CH₃S- | Benzene | 3H | 75.6° C. | 82.0% |

TABLE 9

Succinimides

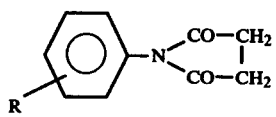

| Examples | R | Solvent used | Reaction time | Melting point °C. | Yield |
|---|---|---|---|---|---|
| 69 | 2,6-dichloro-4-methyl (Cl, CH₃, Cl) | Toluene | 2H | 159.2° C. | ≈100% |
| 70 | 2-bromo-6-isopropyl (Br, CH(CH₃)₂) | Toluene | 2H | 92.1° C. | 89.5% |

TABLE 9-continued
Succinimides

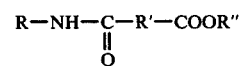

| Examples | R | Solvent used | Reaction time | Melting point °C. | Yield |
|---|---|---|---|---|---|
| 71 | Cl, Cl, CH₃ | Toluene | 2H | 143.0° C. | ≃100% |
| 72 | Br, CH₃, CH₃, CH₃ | Toluene | 2H | 135.9° C. | 56.3% |
| 73 | Cl, CH₃, CH₃, CH₃ | Toluene | 6H 25 | 220.2° C. | 80.4% |
| 74 | Cl, CH₃, Br, CH₃, CH₃, Br, CH₃ | Toluene | 3H | 195.1° C. | 80.0% |

All of the above examples clearly illustrate the remarkable properties of the process of the invention due to the great power of the new type of catalyst used, namely:

very high yields a high purity of the crude product obtained, so that it is possible to avoid subsequent purification very short times of reaction even when large quantities are employed great ease in operation and therefore great reliability high degree of reproducibility of the above advantages whether one operates on a laboratory scale or in large quantities.

We claim:

1. In a process of preparing an imide substituted on the nitrogen having the formula

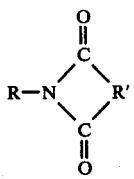

in which R is an alkyl radical containing 1 to 8 carbon atoms, or an aryl radical having 1 or 2 phenyl rings bearing up to 5 substituents selected from the group consisting of 1 to 3 atoms of halogen, 1 to 2 nitro, amino, or hydroxy groups, 1 to 4 alkyl radicals, and 1 to 2 alkoxy or alkylthio radicals, each containing 1 to 4 carbon atoms, or a hexyl radical, R' is a single bond or a hydrocarbon chain containing from 1 to 4 carbon atoms, in which two contiguous carbons may belong to a phenyl ring, said hydrocarbon chain being saturated or unsaturated by cyclization of an amic acid of the formula:

$$R-NH-\underset{\underset{O}{\|}}{C}-R'-COOR''$$

in which

R and R' have the same meaning as above and

R'' is a hydrogen atom, an alkaline metal atom, an ammonium group, or a lower alkyl having 1 to 4 carbon atoms, in accordance with the equation:

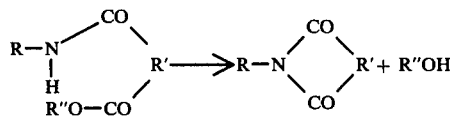

the improvement comprising carrying out the cyclization reaction in the presence of a mixed catalyst resulting from the association of the formula

A B in which A is a strong inorganic or organic acid and B is a Lewis base selected from a member of the group consisting of monomethylformamide, dimethylformamide, monoethylformamide, dimethylacetamide, acetone, acetonitrile, N-methylpyrrolidone, dimethylsulfoxide, mesityl oxide, dioxane and tetrahydrofuran.

2. Process of preparation according to claim 1, in which A is a mono or poly-acid of a pK in water of at most 3.

3. Process for the preparation of an imide substituted on the nitrogen in accordance with claim 2, in which A is selected from the group which consists of sulfuric acid, an organosulfonic acid, phosphoric acid, an organophosphoric acid, and a mono- or dicarboxylic acid, optionally halogenated, containing 1 to 4 carbon atoms.

4. Process of preparation according to claim 3, in which A is sulfuric acid or paratoluene 5. Process according to claim 3, in which A is phosphoric acid.

6. Process according to claim 3, in which A is trifluoroacetic acid.

7. Process of preparation according to claim 3, in which A is maleic acid.

8. Process according to claim 1, in which the molar ratio of the acid to the amic acid is between 0.01 and 10.

9. Process according to claim 8, in which the molar ratio of the acid to the amic acid is between 0.1 and 1.

10. Process according to claim 1, in which the molar ratio of the Lewis base to the amic acid is between 0.01 and 1.

11. Process of preparation according to claim 1, in which the base/acid molar ratio is between 1 and 2.

12. Process according to claim 11 in which the base/acid molar ratio is equal to 1.

13. Process according to claim 11 in which the base/acid molar ratio is equal to 2.

14. Process according to claim 1, in which the catalyst is added in the amount of a catalyst/amic acid molar ratio of between 0.025 and 2.

15. Process according to claim 14, in which the catalyst is added in the amount of a catalyst/amic acid molar ratio of between 0.05 and 0.5.

16. Process according to claim 12 in which a 1:1 $H_2SO_4$/DMF complex is used.

17. Process according to claim 12, in which a 1:2 $H_2SO_4$/DMF complex is used.

18. Process according to claim 3, in which an $H_2SO_4$/N-methylpyrrolidone complex is used.

19. Process according to claim 4 in which an $H_2SO_4$/acetonitrile complex is used.

20. Process according to claim 4 in which an $H_2SO_4$/acetone complex is used.

21. Process according to claim 12 in which a 1:1 paratoluene sulfonic acid/DMF complex is used.

22. Process according to claim 1 in which the reaction is carried out without solvent.

23. Process according to claim 1 in which the reaction is carried out in an inert solvent medium of a boiling point of between 80° and 180° C.

24. Process according to claim 23, in which the solvent is an aromatic solvent.

25. Process according to claim 23, in which the solvent is toluene.

26. Process according to claim 23, in which the solvent is xylene.

27. Process according to claim 1 in which the reaction is carried out for half an hour to six hours.

28. Process according to claim 1 in which the reaction is carried out at a temperature of between 80° and 180° C.

29. Process of preparation according to claim 28, in which the reaction is carried out at a temperature of between 100° and 150° C.

* * * * *